United States Patent [19]

Nakashima et al.

[11] Patent Number: 5,730,902
[45] Date of Patent: Mar. 24, 1998

[54] OPTICALLY ACTIVE SILACYCLOHEXANE COMPOUNDS, LIQUID CRYSTAL COMPOSITIONS COMPRISING THE SAME AND LIQUID CRYSTAL DISPLAY DEVICES COMPRISING THE COMPOSITIONS

[75] Inventors: Mutsuo Nakashima; Takaaki Shimizu; Tsutomu Ogihara; Tatsushi Kaneko, all of Niigata-ken, Japan

[73] Assignee: Shin-Etsu Chemical Co., Ltd., Tokyo, Japan

[21] Appl. No.: 700,970

[22] Filed: Aug. 21, 1996

[30] Foreign Application Priority Data

Aug. 28, 1995 [JP] Japan .................................. 7-242515

[51] Int. Cl.⁶ ........................ C09K 19/34; C09K 19/30; C07F 7/08
[52] U.S. Cl. ................. 252/299.61; 252/299.63; 252/299.66; 556/406
[58] Field of Search ............... 252/299.01, 299.63, 252/299.66, 299.61; 556/406

[56] References Cited

U.S. PATENT DOCUMENTS 5,454,977  10/1995  Shimizu et al. ................... 252/299.61

FOREIGN PATENT DOCUMENTS

| 0630903 | 12/1994 | European Pat. Off. . |
| 0632044 | 1/1995 | European Pat. Off. . |
| 0657460 | 6/1995 | European Pat. Off. . |
| 0718301 | 6/1996 | European Pat. Off. . |
| 4322905 | 1/1994 | Germany . |

*Primary Examiner*—Shean C. Wu
*Attorney, Agent, or Firm*—Lowe, Price, LeBlanc & Becker

[57] ABSTRACT

An optically active silacyclohexane compound of the formula (I)

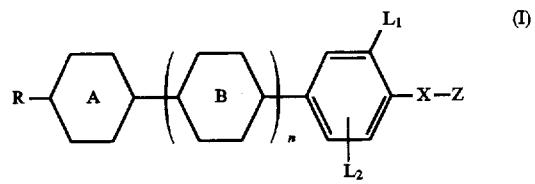

wherein R represents an organic residue, X represents —$CH_2$— or —O—; Z represents a chiral group having at least one chiral carbon atom; $L_1$ and $L_2$ independently represent H or F, n is 0 or 1;

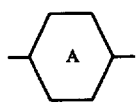

represents a trans-1-sila-1,4-cyclohexylene group or trans-4-sila-1,4-cyclohexylene group whose silicon atom at the 1 or 4 position has H, F, Cl or $CH_3$, or a 1,4-cyclohexylene group; and

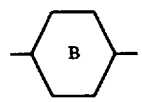

represents a trans-1-sila-1,4-cyclohexylene group or trans-4-sila-1,4-cyclohexylene group whose silicon atom at the 1 or 4 position has H, F, Cl or $CH_3$, a 1,4-cyclohexylene group or a 1,4-phenylene group provided that at least one of

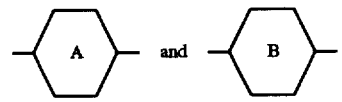

represents the trans-1-sila-1,4-cyclohexylene group or trans-4-sila-1,4-cyclohexylene group defined above. A liquid crystal composition comprising the compound defined above and a liquid crystal display device comprising the composition are also described.

15 Claims, No Drawings

OPTICALLY ACTIVE SILACYCLOHEXANE COMPOUNDS, LIQUID CRYSTAL COMPOSITIONS COMPRISING THE SAME AND LIQUID CRYSTAL DISPLAY DEVICES COMPRISING THE COMPOSITIONS

BACKGROUND OF THE INVENTION

1. Field of The Invention

This invention relates to novel silacyclohexane compounds having a chiral group. The invention also relates to a liquid crystal composition comprising the silacyclohexane compound and to a device comprising the composition.

2. Description of the Prior Art

The liquid crystal display devices make use of optical anisotropy and dielectric anisotropy of liquid crystal substances. Depending on the mode of display, a variety of display systems are known including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the Schadt-Helfrich effect and has a twisted nematic structure.

The liquid crystal compositions which are employed in the twisted nematic structure are usually admixed with a small amount an optically active substance for controlling the twisting direction in order to prevent display deficiencies such as reverse tilt discrimination. The optically active substances known in the art include liquid crystal compounds having a cholesteric phase, e.g. compounds having ester groups such as cholesteryl nonanoate, phenyl benzoate and the like, or compounds of the following formulas C₃H₇—H—H—〈F, CH₃, OCHC₆H₁₃, F〉, and

C₃H₇—H—H—〈F, CH₃, CH₂CHC₂H₅, F〉

These compounds are set out in Japanese Laid-open patent Application No. 6-206837.

As liquid crystal panels recently become advanced in performance, there arises the problem that the optically active substances adversely influence panel characteristics, e.g. they act to lower potential retention and to increase saturation voltage.

SUMMARY OF THE INVENTION

It is an object of the invention to provide a novel, optically active silacyclohexane compound which can overcome the problem of the prior art optically active substances.

It is another object of the invention to provide a novel silacyclohexane compound serving as a liquid crystal compound which has at least one silacyclohexane ring containing a silicon atom in the molecule.

It is a further object of the invention to provide a liquid crystal composition which comprises at least one compound of the type as set out above and also a liquid crystal display device comprising the composition.

The above object can be achieved, according to the invention, by an optically active silacyclohexane compound of the formula (I)

R—(A)—(B)ₙ—〈L₁, X—Z, L₂〉 (I)

wherein R represents a linear alkyl group having from 1 to 10 carbon atoms, a branched alkyl group having from 3 to 8 carbon atoms, an alkoxyalkyl group having from 2 to 7 carbon atoms, a mono or difluoroalkyl group having from 1 to 10 carbon atoms, or an alkenyl group having from 2 to 8 carbon atoms; X represents —CH₂— or —O—; Z represents a chiral group having at least one chiral carbon atom; L₁ and L₂ independently represent H or F, n is 0 or 1;

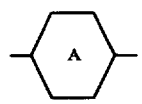

represents a trans-1-sila-1,4-cyclohexylene group or trans-4-sila-1,4-cyclohexylene group whose silicon atom at the 1 or 4 position has H, F, Cl or CH₃, or a 1,4-cyclohexylene group; and

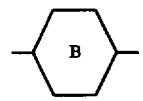

represents a trans-1-sila-1,4-cyclohexylene group or trans-4-sila-1,4-cyclohexylene group whose silicon atom at the 1 or 4 position has H, F, Cl or CH₃, a 1,4-cyclohexylene group or a 1,4-phenylene group provided that the silacyclohexane compound has at least one of the trans-1-sila-1,4-cyclohexylene group and the trans-4-sila-1,4-cyclohexylene group, i.e. at least one of

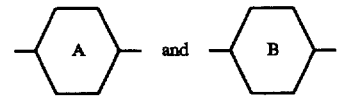

represents the trans-1-sila-1,4-cyclohexylene group or trans-4-sila-1,4-cyclohexylene group defined above.

According to the invention, there is also provided a liquid crystal composition which comprises the silacyclohexane compound of the type mentioned above along with a liquid crystal display device which comprises the composition.

DETAILED DESCRIPTION OF THE INVENTION

The novel compounds of the formula (I) are silacyclohexane compounds which have a trans-1-silacyclohexane and/or trans-4-silacyclohexane ring structure as particularly shown in the formulas (Ia) to (Ik):

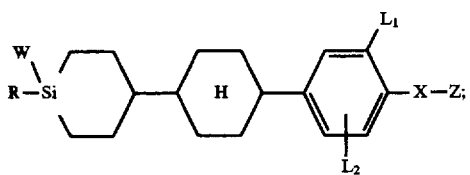 (Ia)

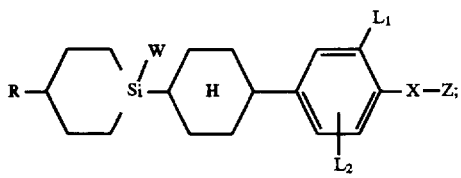 (Ib)

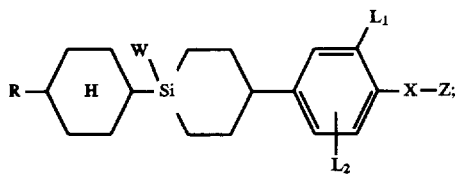 (Ic)

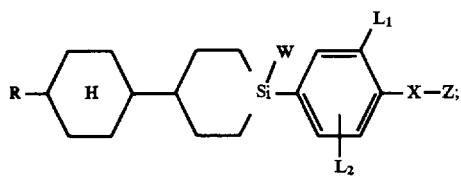 (Id)

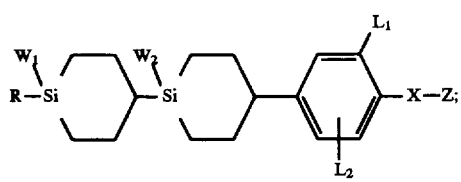 (Ie)

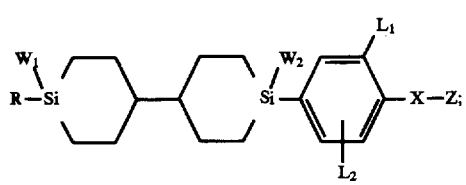 (If)

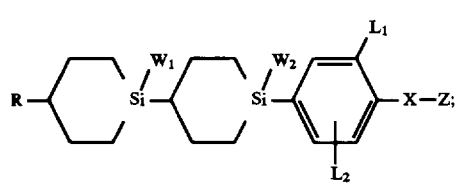 (Ig)

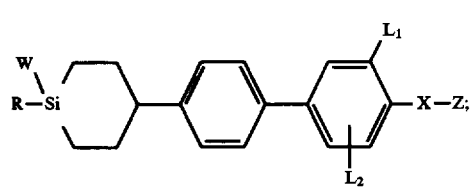 (Ih)

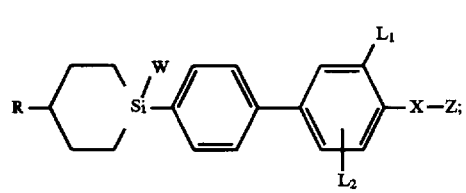 (Ii)

-continued

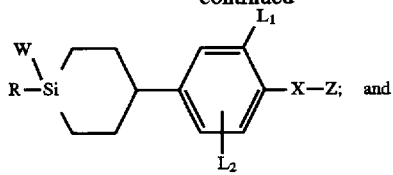 (Ij)

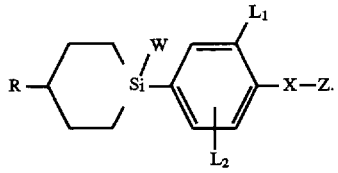 (Ik)

In the general formulas (I) and (Ia) to (Ik), R represents a linear alkyl group having from 1 to 10 carbon atoms, a branched alkyl group having from 3 to 8 carbon atoms, an alkoxyalkyl group having from 2 to 7 carbon atoms, a mono or difluoroalkyl group having from 1 to 10 carbon atoms, or an alkenyl group having from 2 to 8 carbon atoms.

Specific examples of the linear alkyl group include methyl, ethyl, n-propyl, n-butyl, n-pentyl, n-hexyl, n-heptyl, n-octyl, n-nonyl and n-decyl.

Specific examples of the branched alkyl group include isopropyl, secbutyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl.

Specific examples of the alkoxyalkyl group include methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl, ethoxypentyl and methoxyhexyl.

Specific examples of the mono or difluoroalkyl group include fluoromethyl, 1-fluoromethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 8-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl and 10,10-difluorodecyl.

Specific examples of the alkenyl group include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl and 7-octenyl.

In the formulas, W, $W_1$ and $W_2$ independently represent H, F, Cl or $CH_3$.

X represents $—CH_2—$ or $—O—$, $L_1$ and $L_2$ independently represent H or F. Z represents a chiral group containing at least one chiral carbon atom. The chiral group is one which is of the formula (IIa), (IIb) or (IIc):

(IIa)

wherein p is 0 or an integer of from 1 to 8, q is an integer of from 2 to 14, $R_0$ represents hydrogen or a linear alkyl group having from 1 to 6 carbon atoms, Y represents $CH_3$, a halogen, i.e. Cl, Br, F or I, $CF_3$, $CHF_2$, $CH_2F$ or CN, and C* is a chiral carbon atom having four different substituents, so that $R_0$, Y and $—C_qH_{2q+1}$ should be different from each other;

(IIb)

wherein r is 0 or an integer of 1 to 8, s is 0 or an integer of 1 to 6, and m is an integer of from 1 to 10; or

(IIc)

wherein r and m are, respectively, as defined in (IIb).

Among the silacyclohexane compounds of the formulas (Ia) to (Ik), those compounds of the formulas (Ia), (Ic), (Ie), (Ih) and (Ij) are preferred.

Preferred groups represented by R include: linear alkyl groups having from 2 to 7 carbon atoms, such as ethyl, n-propyl, n-butyl, n-pentyl, n-hexyl and n-heptyl; branched alkyl groups having from 3 to 8 carbon atoms, such as isopropyl, sec-butyl, iso-butyl, 1-methylbutyl, 2-methylbutyl, 3-methylbutyl, 1-methylpentyl, 2-methylpentyl and 2-ethylhexyl; alkoxyalkyl groups having from 2 to 6 carbon atoms, such as methoxymethyl, ethoxymethyl, propoxymethyl, pentoxymethyl, methoxyethyl, ethoxyethyl, methoxypropyl and methoxypentyl; mono or difluoroalkyl groups having from 2 to 7 carbon atoms, such as 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoropentyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl; and alkenyl groups having from 2 to 8 carbon atoms, such as vinyl, 1-pentenyl, 3-butenyl, 1-pentenyl, 3-pentenyl, 4-pentenyl, 1-hexenyl, 5-hexenyl, 6-heptenyl and 7-octenyl.

W, $W_1$ and $W_2$ should preferably be H, F or $CH_3$, respectively.

Preferred chiral groups represented by Z include the group of the formula (IIa) wherein p is 0, 1 or 2, q is an integer of from 2 to 10, $R_0$ is hydrogen, and Y represents $CH_3$, F or CN, and groups of the formulas (IIb) and (IIc).

The moiety of the formula (1)

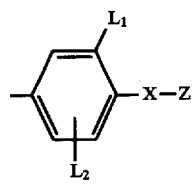
(1)

includes those indicated below:

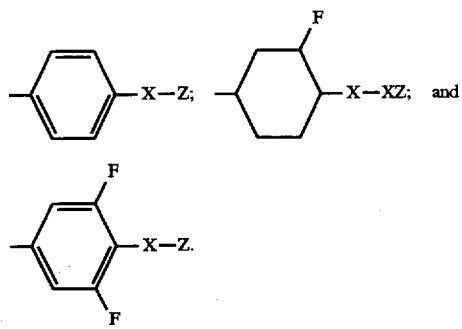

Of these, the last one is preferred.

The preparation of the silacyclohexane compound of the general formula (I) is described.

The silacyclohexane compounds of the formula (I) can be prepared from intermediate compounds of the following formulas (A) and (B), which, respectively, have ring structures corresponding to those of the compounds of the formula (Ia) to (Ik) and whose preparations are known in the art:

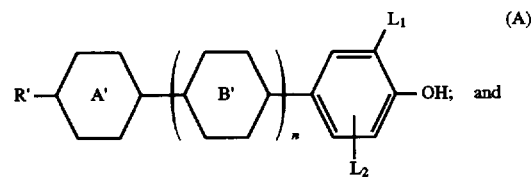
(A)

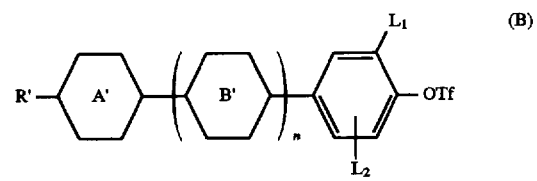
(B)

wherein n, $L_1$ and $L_2$ are, respectively, as defined before,

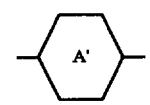

represents a trans-1-sila-1,4-cyclohexylene group or trans-4-sila-1,4-cyclohexylene group whose silicon atom at the 1 or 4 position has phenyl or tolyl, or a 1,4-cyclohexylene group; and

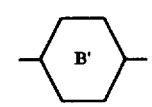

represents a trans-1-sila-1,4-cyclohexylene group or trans-4-sila-1,4-cyclohexylene group whose silicon atom at the 1 or 4 position has phenyl or tolyl, a 1,4-cyclohexylene group or a 1,4-phenylene group provided that at least one of

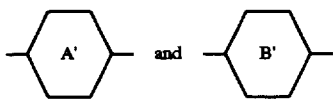 and 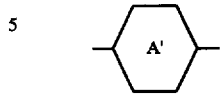

represents the trans-1-sila-1,4-cyclohexylene group or trans-4-sila-1,4-cyclohexylene group defined above, Tf represents a trifluoromethanesulfonyl group (—SO$_2$CF$_3$), and R' represents R or Ar in which Ar represents phenyl or tolyl.

(i) Compounds of the formula (I) wherein X is —O— are prepared according to the following reaction sequence (IIIa) provided that the substituent attached to

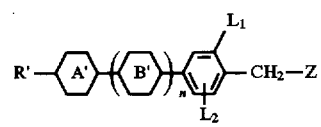

is R'

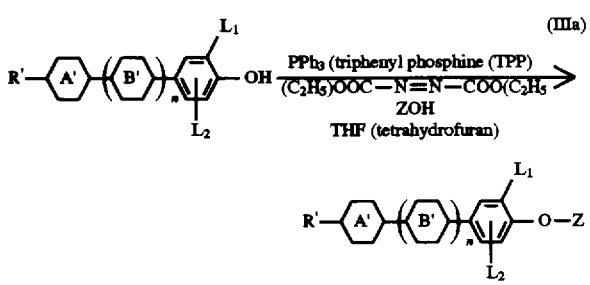

wherein Z is same as defined in the formula (I).

(ii) Compounds of the formula (I) wherein X is —CH$_2$— are prepared according to the following reaction sequence (IIIb) provided that the substituent attached to

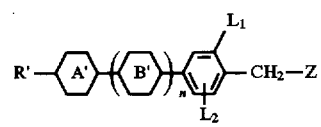

is R'

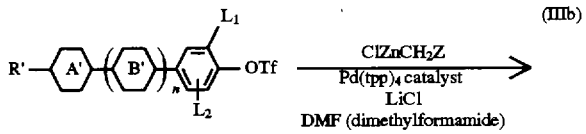

wherein tpp represents triphenyl phosphine.

The compounds of the general formulas (IIIa) and (IIIb) are arylsilacyclohexane compounds as expressed by the general formulas (Ia) to (Ik) wherein W, W$_1$ and W$_2$ are, respectively, Ar defined before and R' is R. These arylsilacyclohexane compounds can be converted to chlorosilacyclohexane, fluorosilacyclohexane, methylsilacyclohexane and hydrosilacyclohexane compounds according to the following reaction sequence wherein the related moieties alone are shown:

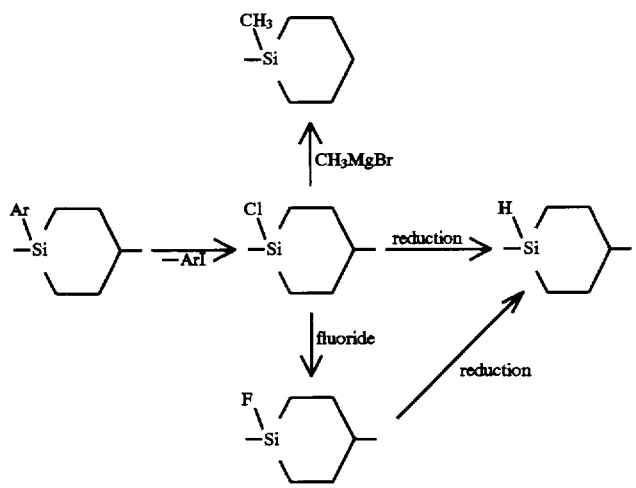

The above reaction sequence is illustrated. When iodine monochloride is reacted with arylsilacyclohexane compounds (corresponding to compounds of the general formulas (Ia) to (Ik) wherein W, W$_1$ and W$_2$ are, respectively, Ar), corresponding chlorosilacyclohexane compounds, i.e. compounds of the general formulas (Ia) to (Ik) wherein W, W$_1$ and W$_2$, are, respectively, Cl are obtained.

When the thus obtained chlorosilacyclohexane compounds are reacted with fluorides such as cesium fluoride, copper (I) fluoride, antimony fluoride, calcium fluoride, tetrabutylammonium fluoride and the like, corresponding fluorosilacyclohexane compounds, i.e. compounds of the general formulas (Ia) to (Ik) wherein W, W$_1$ and W$_2$ are, respectively, F, are obtained.

Alternatively, when the chlorosilacyclohexane compounds are reacted with a methyl Grignard reagent, methylsilacyclohexane compounds, i.e. compounds of the formulas (Ia) to (Ik) wherein W, $W_1$ and $W_2$ are, respectively, methyl, are obtained.

Still alternatively, when the chlorosilacyclohexane compounds or fluorosilacyclohexane compounds are reacted, under mild conditions, with metal hydrides such as sodium hydride, calcium hydride, trialkylsilanes, boranes, dialkylaluminium compounds and the like, and/or complex hydrides such as lithium aluminium hydride, sodium borohydride, lithium borohydride, potassium borohydride, tributylammonium borohydride and the like, corresponding hydrosilacyclohexane compounds, i.e. compounds of the formulas (Ia) to (Ik) wherein W, $W_1$ and $W_2$ are, respectively, H, are obtained.

In the intermediate compounds of the formulas (A) and (B) wherein W, $W_1$ and $W_2$ are, respectively, Ar and R' is Ar wherein Ar is phenyl or tolyl, these compounds are, respectively, converted to compounds of the formulas (IIIa) and (IIIb). Thereafter, the compounds of the formulas (IIIa) and (IIIb) are subjected to halo-de-silylation with electrophilic reagents, followed by reduction and monohalogenation to obtain hydrohalogenosilane compounds. Subsequently, the resultant compounds are reacted with Grignard reagents to obtain hydrosilacyclohexane compounds, i.e. compounds of the formulas (Ia) to (Ik) wherein W, $W_1$ and $W_2$ are, respectively, H.

Preparation of the compounds of the formulas (Ia) to (Ik) wherein W, $W_1$ and $W_2$ are, respectively, H from the intermediate compounds of the formulas (A) and (B) wherein W, $W_1$ and $W_2$ are, respectively, Ar and R' is Ar has been described above. The compounds of the formulas (Ia) to (Ik) wherein W, $W_1$ and $W_2$ are, respectively, an atom or a group other than H are prepared in the following manner:

The chlorosilacyclohexane or fluorosilacyclohexane compound is reacted with such metal hydride or complex hydride as mentioned before to obtain a hydrosilacyclohexane compound.

In this manner, in case where R' is Ar, the compounds of the invention can be obtained.

If the thus obtained product consists of a mixture of steric isomers, a trans isomer or a trans-trans isomer is isolated and purified through known purification procedures such as recrystallization, chromatography and the like.

The optically active silacyclohexane compounds of the invention are appropriately used in combination with known liquid crystal compounds to provide liquid crystal compositions. Although other types of liquid crystal compounds may be used, liquid crystal compounds suitable for this purpose include those compounds of the general formulas (IV) to (IX):

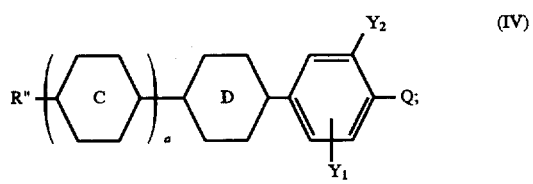

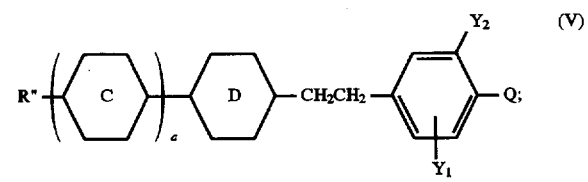

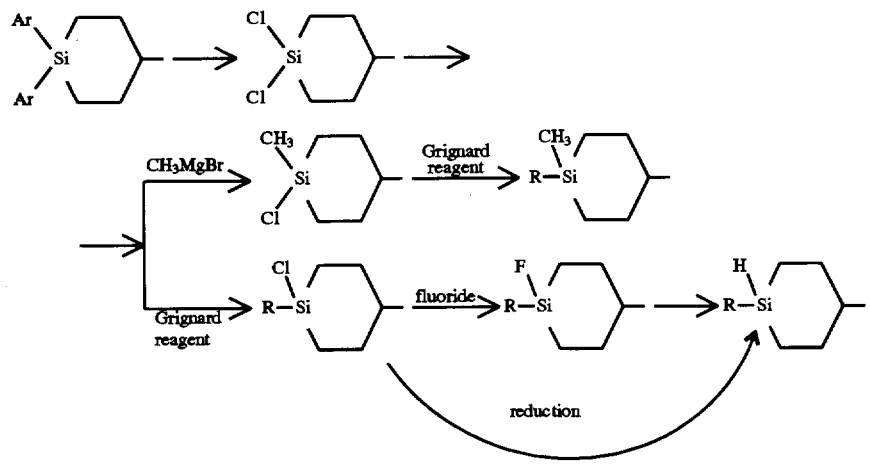

In the above reaction sequence, the diarylsilacyclohexyl group is desilylated with an electrophilic reagent to obtain a dihalogenosilacyclohexyl group.

(1) The dihalogenosilacyclohexyl group is reacted with a methylmagnesium halide such as methylmagnesium bromide to introduce the methyl group, followed by further reaction with a corresponding Grignard reagent to obtain a methylsilacyclohexylene group.

(2) The dihalogenosilacyclohexyl group is reacted with a corresponding Grignard reagent for conversion into a chlorosilacyclohexane group. The chlorosilacyclohexane group may be further converted to a fluorosilacyclohexane group through halogen exchange.

-continued

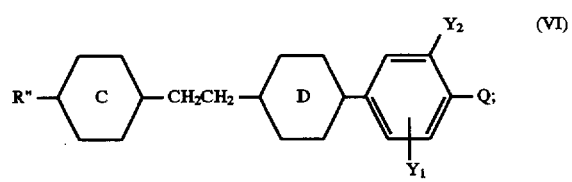

-continued

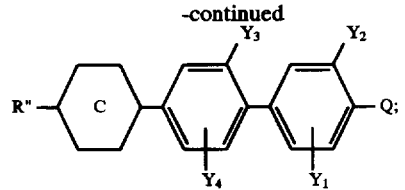

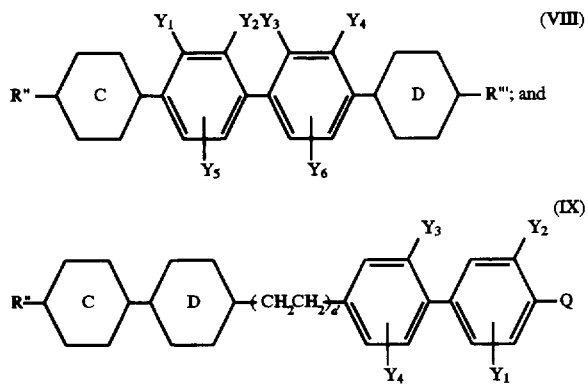

wherein each R" represents an alkyl group having from 2 to 7 carbon an alkoxyalkyl group having from 2 to 7 carbon atoms, a mono or difluoroalkyl group having from 2 to 7 carbon atoms, or an alkenyl group having from 2 to 7 carbon atoms, a and a' are, respectively, 0 or 1,

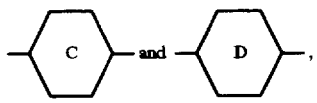

respectively, represent a trans-1-sila-1,4-cyclohexylene group, a trans-4-sila-1,4-cyclohexylene group or a trans-1, 4-cyclohexylene group, Q represents CN, F, Cl, $CF_3$, $OCH_2F$, $CClF_2$, $CHClF$, $OCF_3$, $OClCF_2$, $OCHF_2$, $OCHClF$, $(O)_kCT=CX_1X_2$ wherein k is 0 or 1, T and $X_1$ independently represent H, F or Cl, and $X_2$ represents F or Cl, $O(CH_2)_i(CF_2)_jG$ wherein i and j are, respectively, 0, 1 or 2 provided that i+j=2, 3 or 4, and G represents H, F or Cl, or R" or OR" wherein R" is as defined above, $Y_1$ to $Y_6$ are, respectively, H or F, and R" is same as R". Preferably, Q represents F, Cl, $OCHF_2$, $OCF_3$, $O(CH_2)_i(CF_2)_jG$ or an alkoxy group having not greater than 5 carbon atoms, $O(CH_2)_i(CF_2)_jP$, in which i and j are, respectively, 0, 1 or 2 provided that i+j=2, 3 or 4, and P represents H, or an alkoxy group having not $Y_1$, $Y_2$, $Y_3$, $Y_4$, $Y_5$ and $Y_6$ are, respectively, H or F, and R" is same as R".

These liquid crystal compounds may be used singly or in combination. At least one of the optically active silacyclohexane compounds of the invention should preferably be present in a liquid crystal composition in an amount of 0.05 to 5% by mole, more preferably 0.2 to 1% by mole. The liquid crystal composition should preferably comprise 95 to 99.95% by mole of at least one compounds selected from those of the formulas (IV) to (IX). A diversity of the spiral pitches may be established by the addition of the compound depending on the display mode and the liquid crystal cell design and also on the type of host liquid crystal composition. A desired spiral pitch is obtained by controlling the amount of the optically active silacyclohexane compound.

The liquid crystal phase may further comprise additives such as polychromatic dyes for purifying colored guest-host systems, and additives for controlling dielectric anisotropy, viscosity and the alignment of nematic phase, and the like.

The resultant liquid crystal phase or composition is sealingly placed between transparent substrates each having an electrode of a desired shape to provide a liquid crystal display device. If necessary, the device may have various types of undercoatings, overcoatings for controlling the alignment, polarizers, filters and reflective layers as is known in the art. Alternatively, a multi-layer cell may be used. The liquid crystal display device may be used in combination with other types of display devices, semiconductor substrates, and light sources.

With the compounds of the invention whose dielectric anisotropy value of Δε is positive or is close to zero, the liquid crystal display device is driven according to a supertwisted nematic (STN) system, a twisted nematic (TN) system or a guest-host (GH) system. For the compounds whose value of Δε is negative, a dynamics scattering mode (DSM) system, an electrically controlled birefringence (ECB) system, a guest-host (GH) system and the like known in the art may be adopted.

The invention is more particularly described by way of examples. In the examples, the optical rotation, $[\alpha]_D^{25}$, was determined using a Na-D ray (589 nm) as a light source at a temperature, for example, of 25° C. when the superscript indicates 25. The abbreviation "HTP" means helical twist power wherein twisting in the right direction is expressed as "+" and twisting in the left direction is as "−".

EXAMPLE 1

Preparation of S-(−)-4-(trans-4-(trans-4-n-pentyl-4-silacyclohexyl)cyclohexyl)-1-(1-methylheptyloxy)-2,6-difluorobenzene 4.4 g (25 mmols) of diethylazodicarboxylate was dropped under ice-cooling conditions in a mixture of 9.1 g (20 mmols) of 4-(trans-4-(4-pentyl-4-phenyl-4-silacyclohexyl) cyclohexyl)-2,6-difluorophenol, 2.6 g (20 mmols) of R-(−)-2-octanol, 6.6 g (25 mmols) of triphenylphosphine and 50 ml of tetrahydrofuran (hereinafter referred to simply as THF), followed by agitation for 2 hours. The reaction mixture was after-treated by a usual manner and purified through chromatography to obtain 9.2 g (yield: 82%) of 4-(trans-4-(4-n-pentyl-4-phenyl-4-silacyclohexyl) cyclohexyl)-1-(1-methylheptyloxy)-2,6-difluorobenzene.

The results of IR and NMR analyses are shown below. IR (liquid film) $v_{max}$: 2924, 2856, 1585, 1514, 1240, 1113, 1024, 926, 849 $cm^{-1}$ $^1$H-NMR (CDCl$_3$) δ: 0.5–2.5 (46H, m), 4.1–4.4 (1H, m), 6.6–7.0 (2H), 7.3–7.6 (5H) ppm 2.5 ml of a carbon tetrachloride solution of 1.0 mole of iodine monochloride was added to a mixture of 1.14 g (2.0 mmols) of the difluorobenzene product and 15 ml of carbon tetrachloride at room temperature, and agitated for 1 hour. The reaction mixture was concentrated under reduced pressure to obtain 1.00 g (yield: 95%) of 4-(trans-4-(4-n-pentyl-4-chloro-4-silacyclohexyl)cyclohexyl)-1-(1methylheptyloxy)-2,6-difluorobenzene.

0.53 g (1.00 mmol) of the thus obtained product was added to a mixture of 100 mg of lithium aluminium hydride and 20 ml of THF and agitated at −20° C. for 15 minutes. The reaction mixture was charged into dilute hydrochloric acid, followed by after-treatment by a usual manner. The resultant crude product was found to consist of a mixture of trans and cis isomers with respect to the cyclohexane ring, and these isomers were separated from each other through chromatography to obtain 0.34 g (yield: 70%) of an intended trans-trans isomer. The physical properties of the isomer are shown below.

$T_{SI}$ (smectic phase to isotropic phase transition temperature)=46° C. IR (KBr, disc) $v_{max}$: 2924, 2852, 2100, 1585, 1514, 1441, 1336, 1240, 1024, 887, 845, 818 cm$^{-1}$ [α]$_D^{26}$=−6.3 (CHCl$_3$)

HTP=+10.4 (10% of a sample was mixed with ZLI-2293 (commercial name of Merck & CO., Inc.) and subjected to measurement of HTP).

EXAMPLE 2

Preparation of (R)-4-(trans-4-(trans-4-n-propyl-4-silacyclohexyl)cyclohexyl)-1-(1-methylbutyloxy)-2,6-difluorobenzene The general procedure of Example 1 was repeated using 4-(trans-4-(4-n-propyl-4-phenyl-4-silacyclohexyl) cyclohexyl)-2,6-difluorophenol and (R)-2-pentanol, thereby obtaining the intended compound. The physical properties of the compound are shown below.

$T_{CS}$ (crystal to smectic phase transition temperature)=17° C. $T_{SCH}$ (smectic to cholesteric phase transition temperature)=41° C. $T_{CHI}$ (cholesteric to isotropic phase transition temperature)=64° C. HTP=−13.9 (determined as in Example 1)

EXAMPLE 3

Preparation of (R)-(+)-4-(trans-4-(trans-4-n-pentyl-4-silacyclohexyl)cyclohexyl)-1-(heptyloxy)-2,6-difluorobenzene The general procedure of Example 1 was repeated using 4-(trans-4-(4-n-pentyl-4-phenyl-4-silacyclohexyl) cyclohexyl)-2,6-difluorophenol and (S)-2-octanol, thereby obtaining the intended compound. The physical properties of the compound are shown below.

$T_{SI}$=46° C. IR (KBr, disc) $v_{max}$: 2924, 2852, 2100, 1585, 1514, 1441, 1336, 1240, 1024, 887, 845, 818 cm$^{-1}$ [α]$_D^{25}$= 6.3 (CHCl$_3$)

HTP=−10.2 (10% of a sample was mixed with ZLI-2293 and subjected to measurement of HTP).

EXAMPLE 4

Preparation of (R)-4-(trans-4-(trans-4-n-heptylcyclohexyl)-4-silacyclohexyl)-1-(1-methyloctyloxy)-2,6-difluorobenzene The general procedure of Example 1 was repeated using 4-(4-(trans-4-n-heptylcyclohexyl)-4-silacyclohexyl)-2,6-difluorophenol and (S)-2-nonanol, thereby obtaining the intended compound.

EXAMPLE 5

Preparation of (S)-4-(trans-4-(trans-4-n-octylcyclohexyl)-4-silacyclohexyl)-1-(1-methyloctyloxy)-2,6-difluorobenzene The general procedure of Example 1 was repeated using 4-(4-(trans-4-n-octylcyclohexyl)-4-phenyl-4-4-silacyclohexyl)-2,6-difluorophenol and (R)-2-nonanol, thereby obtaining the intended compound.

EXAMPLE 6

Preparation of (R)-4-(4-(trans-4-n-propyl-4-methyl-4-silacyclohexyl)phenyl)-1-(1-methyloctyloxy)-2,6-difluorobenzene The general procedure of Example 1 was repeated using 4-(4-(4-n-propyl-4-methyl-4-silacyclohexyl)phenyl)-2,6-difluorophenol and (S)-2-nonanol, thereby obtaining the intended compound. cl EXAMPLE 7

Preparation of (S)-4-(4-(trans-4-n-pentyl-4-silacyclohexyl)phenyl)-1-(1-methyloctyloxy)-2,6-difluorobenzene The general procedure of Example 1 was repeated using 4-(4-(4-n-pentyl-4-phenyl-4-silacyclohexyl)phenyl) -2,6-difluorophenol and (R)-2-nonanol, thereby obtaining the intended compound. The physical properties of the compound are shown below.

$T_{CI}$ (crystal phase to isotropic phase transition temperature)=14° C. $T_{SI}$=0° C. [α]$_D^{30}$=−11.3 (CHCl$_3$) HTP=+9.4 (10% of a sample was mixed with ZLI-2293 and subjected to measurement of HTP).

EXAMPLE 8

Preparation of (S)-4-(4-(trans-4-n-heptyl-4-silacyclohexyl)phenyl)-1-(1-methyloctyloxy)-2,6-difluorobenzene The general procedure of Example 1 was repeated using 4-(4-(4-n-heptyl-4-phenyl-4-silacyclohexyl)phenyl) -2,6-difluorophenol and (R)-2-nonanol, thereby obtaining the intended compound.

EXAMPLE 9

Preparation of (R)-4-(4-(trans-4-(4-fluoropentyl)-4-silacyclohexyl)phenyl)-1-(1-methyloctyloxy)-2,6-difluorobenzene The general procedure of Example 1 was repeated using 4-(4-(4-fluoropentyl)-4-phenyl-4-silacyclohexyl) phenyl)-2,6-difluorophenol and (S)-2-nonanol, thereby obtaining the intended compound.

EXAMPLE 10

Preparation of (R)-4-(trans-4-(trans-4-n-propyl-4-silacyclohexyl)cyclohexyl)-1-(2-fluorooctyloxy)-2,6-difluorobenzene The general procedure of Example 1 was repeated using 4-(trans-4-(4-n-propyl-4-phenyl-4-silacyclohexyl) phenyl)-2,6-difluorophenol and (S)-2-fluoro-1-oxtanol, thereby obtaining the intended compound.

EXAMPLE 11

Preparation of (S)-4-(trans-4-(trans-4-n-pentyl-4-silacyclohexyl)cyclohexyl)-1-(2-fluorooctyloxy)-2,6-difluorobenzene The general procedure of Example 1 was repeated using 4-(trans-4-(4-n-pentyl-4-phenyl-4-silacyclohexyl) cyclohexyl)-2,6-difluorophenol and (S)-2-fluoro-1-octanol, thereby obtaining the intended compound.

EXAMPLE 12

Preparation of (S)-4-(trans-4-(trans-4-n-heptylcyclohexyl)-4-fluoro-4-silacyclohexyl)-1-(2-fluorodecyloxy)-2,6-difluorobenzene The general procedure of Example 1 was repeated using 4-(4-trans-4-n-heptylcyclohexyl)-4-fluoro-4-silacyclohexyl)-2,6-difluorophenol and (R)-2-fluoro-1-decanol, thereby obtaining the intended compound.

EXAMPLE 13

Preparation of (R)-4-(trans-4-(trans-4-(3-methylbutyl)cyclohexyl)-4-silacyclohexyl)-1-(2-fluorodecyloxy)-2,6-difluorobenzene The general procedure of Example 1 was repeated using 4-(4-(trans-4-(3-methylbutyl)cyclohexyl)-4-phenyl-4-silacyclohexyl)-2,6-difluorophenol and (S)-2-fluoro-1-decanol, thereby obtaining the intended compound.

EXAMPLE 14

Preparation of (R)-4-(4-(trans-4-n-propyl-4-silacyclohexyl)phenyl)-1-(2-fluorooctyloxy)2,6-difluorobenzene The general procedure of Example 1 was repeated using 4-(4-(4-n-propyl-4-phenyl-4-silacyclohexyl)phenyl) -2,6-difluorophenol and (S)-2-fluoro-1-octanol, thereby obtaining the intended compound.

EXAMPLE 15

Preparation of (R)-4-(4-(trans-4-n-pentyl-4-silacyclohexyl)phenyl)-1-(2-fluorodecyloxy)-2,6-difluorobenzene The general procedure of Example 1 was repeated using 4-(4-(4-n-pentyl-4-phenyl-4-silacyclohexyl)phenyl) -2,6-difluorophenol and (S)-2-fluoro-1-decanol, thereby obtaining the intended compound.

EXAMPLE 16

Preparation of (S)-4-(4-(trans-4-n-nonyl-4-silacyclohexyl)phenyl)-1-(2-fluorooctyloxy)-2,6-difluorobenzene The general procedure of Example 1 was repeated using 4-(4-(4-n-nonyl-4-phenyl-4-silacyclohexyl)phenyl) -2,6-difluorophenol and (R)-2-fluoro-1-octanol, thereby obtaining the intended compound.

EXAMPLE 17

Preparation of (S)-4-(4-(trans-4-(4-bromobutyl)-4-silacyclohexyl)phenyl)-1-(2-fluorononyloxy) -2,6-difluorobenzene The general procedure of Example 1 was repeated using 4-(4-(4-(4-fluorobutyl)-4-phenyl-4-silacyclohexyl)phenyl)-2,6-difluorophenol and (R)-3-fluoro-1-nonanol, thereby obtaining the intended compound.

EXAMPLE 18

Preparation of (S)-4-(trans-4-n-heptyl-4-silacyclohexyl)-1-(2-methylbutyl)-2,6-difluorobenzene 3.0 g (20 mmols) of (S)-1-bromo-2-methylbutane was dropped in a mixture of 0.5 g (21 mmols) of magnesium and 50 ml of THF to obtain a Grignard reagent. This reagent was dropped in 20 ml of a THF solution of 2.8 g (20 mmols) of zinc chloride to obtain an organizing reagent. Subsequently, the solution was dropped in a mixture of 10.7 g (20 mmols) of (2,6-difluoro-4-(4-n-heptyl-4-phenyl-4-silacyclohexyl) phenyl) trifluoromethanesulfonate, 100 mg of tetrakis (triphenylphosphine)palladium (0), 500 mg of lithium chloride and 50 ml of N,N-dimethylformamide, and agitated at 50° C. for 8 hours. The reaction mixture was after-treated by a usual manner and purified through chromatography to obtain 6.4 g (yield: 70%) of 4-(4-n-heptyl-4-phenyl-4-silacyclohexyl)-1-(2-methylbutyl)-2,6-difluorobenzene.

2.5 ml of a carbon tetrachloride solution of 1.0M of iodine monochloride was added to a mixture of 0.91 g (1.0 mmols) of the thus obtained difluorobenzene product and 15 ml of carbon tetrachloride at room temperature, and agitated for 1 hour. The reaction mixture was concentrated under reduced pressure to obtain 0.80 g (yield: 96%) of 4-(4-n-heptyl-4-chloro-4-silacyclohexyl)-1-(2-methylbutyl)-2,6-difluorobenzene.

0.42 g (1.0 mmol) of the resultant product was added to a mixture of 100 mg of lithium air, aluminium hydride and 20 ml of THF, and agitated at −20° C. for 15 minutes. The reaction mixture was charged into dilute hydrochloric acid and after-treated by a usual manner. The resultant crude product was found to consist of a mixture of trans and cis isomers with respect to the silacyclohexane ring, and the isomers were separated from each other through chromatography to obtain 0.32 g (yield: 85%) of the intended trans isomer.

EXAMPLE 19

Preparation of (S)-4-(trans-4-n-pentyl-4-silacyclohexyl)-1-(2-methylbutyl)-2,6-difluorobenzene The general procedure of Example 18 was repeated using (S)-1-bromo-2-methylbutane and (2,6-difluoro-4-(4-n-pentyl-4-phenyl-4-silacyclohexyl)phenyl) trifluoromethanesulfonate, thereby obtaining the intended compound.

EXAMPLE 20

Preparation of (S)-4-(trans-4-n-propyl-4-silacyclohexyl)-1-(2-fluorooctyl)-2,6-difluorobenzene The general procedure of Example 18 was repeated using (S)-1-bromo-2-fluorooctane and (2,6-difluoro-4-(4-n-propyl-4-phenyl-4-silacyclohexyl)phenyl) trifluoromethanesulfonate, thereby obtaining the intended compound.

EXAMPLE 21

Preparation of (R)-4-(trans-4-(4-pentenyl)-4-silacyclohexyl)-1-(2-fluorooctyl)-2,6-difluorobenzene The general procedure of Example 18 was repeated-using (R)-1-bromo-2-fluorooctane and (2,6-difluoro-4-(4-(4-pentenyl)-4-phenyl-4-silacyclohexyl)phenyl) trifluoromethanesulfonate, thereby obtaining the intended compound.

EXAMPLE 22

Preparation of (R)-4-(trans-4-(5-methoxypentyl)-4-silacyclohexyl)-1-(2-fluorooctyl)-2,6-difluorobenzene The general procedure of Example 18 was repeated using (R)-1-bromo-2-fluorooctane and (2,6-difluoro-4-(4-(5-methoxypentyl)-4-phenyl-4-silacyclohexyl)phenyl) trifluoromethanesulfonate, thereby obtaining the intended compound.

EXAMPLE 23

Preparation of (S)-4-(trans-4-(trans-4-n-pentyl-4-silacyclohexyl)cyclohexyl)-1-(1-methylbutyloxy) benzene The general procedure of Example 1 was repeated using 4-(trans-4-(4-n-pentyl-4-phenyl-4-silacyclohexyl) cyclohexyl)phenol and (R)-2-pentanol, thereby obtaining the intended compound.

EXAMPLE 24

Preparation of (S)-4-(trans-4-(trans-4-n-pentyl-4-silacyclohexyl)cyclohexyl)-1-(2- methylbutyl) benzene The general procedure of Example 18 was repeated using (S)-1-bromo-2-methylbutane and (4-(trans-4-(4-n-pentyl-4-phenyl-4-silacyclohexyl)cyclohexyl)phenyl) trifluoromethanesulfonate, thereby obtaining the intended compound.

EXAMPLE 25

Preparation of (R)-4-(4-(trans-4-n-heptyl-4-silacyclohexyl)phenyl)-1-(2-fluoroheptyloxy) benzene The general procedure of Example 1 was repeated using 4-(4-(4-n-heptyl-4-phenyl-4-silacyclohexyl)phenyl) phenol and (S)-2-fluoro-1-heptanol, thereby obtaining the intended compound.

What is claimed is:

1. An optically active silacyclohexane compound of the formula (I)

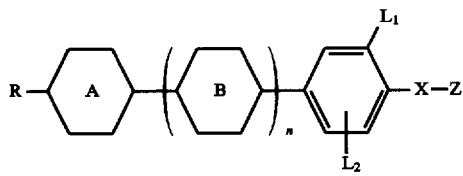

wherein R represents a linear alkyl group having from 1 to 10 carbon atoms, a branched alkyl group having from 3 to 8 carbon atoms, an alkoxyalkyl group having from 2 to 7 carbon atoms, a mono or difluoroalkyl group having from 1 to 10 carbon atoms, or an alkenyl group having from 2 to 8 carbon atoms; X represents —$CH_2$— or —O—; Z represents a chiral group having one to three chiral carbon atoms $L_1$ and $L_2$ independently represent H or F, n is 0 or 1;

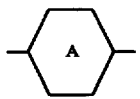

represents a trans-1-sila-1,4-cyclohexylene group or trans-4-sila-1,4-cyclohexylene group whose silicon atom at the 1 or 4 position has H, F, Cl or $CH_3$, or a 1,4-cyclohexylene group; and

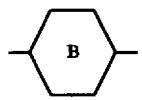

represents a trans-1-sila-1,4-cyclohexylene group or trans-4-sila-1,4-cyclohexylene group whose silicon atom at the 1 or 4 position has H, F, Cl or $CH_3$, a 1,4-cyclohexylene group or a 1,4-phenylene group provided that at least one of

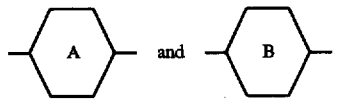

represents the trans-1-sila-1,4-cyclohexylene group or trans-4-sila-1,4-cyclohexylene group defined above.

2. An optically active silacyclohexane compound according to claim 1, wherein said chiral group represented by Z consists of a group of the formula (IIa)

wherein p is 0 or an integer of from 1 to 8, q is an integer of from 2 to 14, $R_0$ represents hydrogen or a linear alkyl group having from 1 to 6 carbon atoms, Y represents $CH_3$, a halogen, $CF_3$, $CHF_2$, $CH_2F$ or CN, and C* is a chiral carbon atom having four different substituents, so that $R_0$, Y and —$C_qH_{2q+1}$ differ from each other.

3. An optically active silacyclohexane compound according to claim 1, wherein said chiral group represented by Z consists of a group of the formula (IIb)

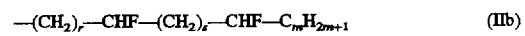

wherein r is 0 or an integer of 1 to 8, s is 0 or an integer of 1 to 6, and m is an integer of from 1 to 10.

4. An optically active silacyclohexane compound according to claim 1, wherein said chiral group represented by Z consists of a group of the formula (IIc)

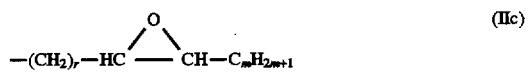

wherein r is 0 or an integer of 1 to 8, and m is an integer of from 1 to 10.

5. An optically active silacyclohexane compound according to claim 1, wherein said compound consists of a compound of the formula (Ia)

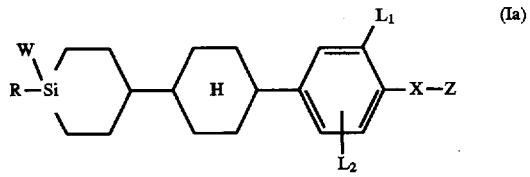

wherein W represents H, F, Cl or $CH_3$.

6. An optically active silacyclohexane compound according to claim 1, wherein said compound consists of a compound of the formula (Ic)

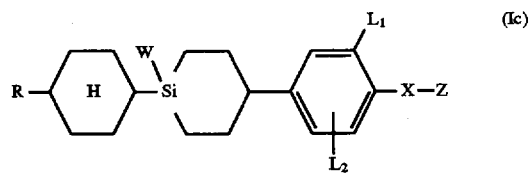

wherein W represents H, F, Cl or $CH_3$.

7. An optically active silacyclohexane compound according to claim 1, wherein said compound consists of a compound of the formula (Ie)

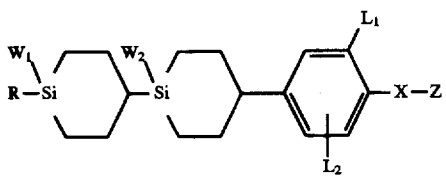

wherein $W_1$ and $W_2$, respectively, represent H, F, Cl or $CH_3$.

8. An optically active silacyclohexane compound according to claim 1, wherein said compound consists of a compound of the formula (Ih)

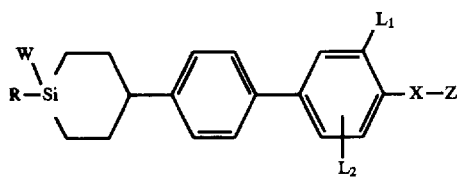

wherein W represents H, F, Cl or $CH_3$.

9. An optically active silacyclohexane compound according to claim 1, wherein said compound consists of a compound of the formula (Ij)

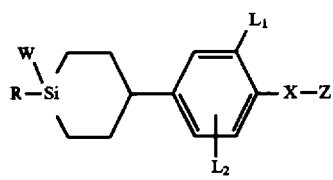

wherein W represents H, F, Cl or $CH_3$.

10. An optically active silacyclohexane compound according to claim 1, wherein the moiety represented by the formula

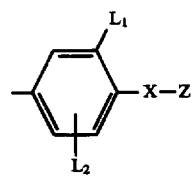

consists of a moiety of the formula,

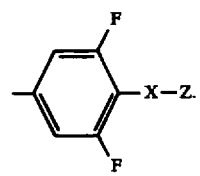

11. A liquid crystal composition which comprises the optically active silacyclohexane compound defined in claim 1.

12. A liquid crystal display device which comprises the composition defined in claim 11.

13. A liquid crystal composition according to claim 11, wherein said optically active silacyclohexane compound is present in an amount of from 0.05 to 5% by mole of the composition.

14. A liquid crystal composition according to claim 11, further comprising at least one compound selected from compounds of the formulas (IV) to (IX)

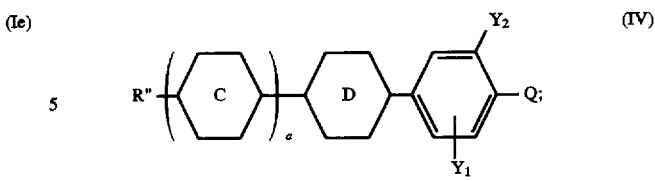

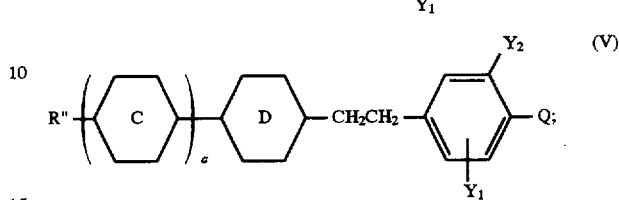

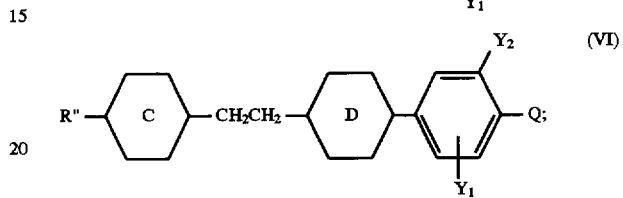

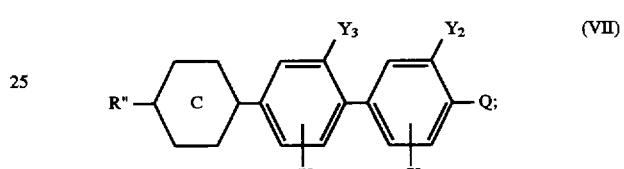

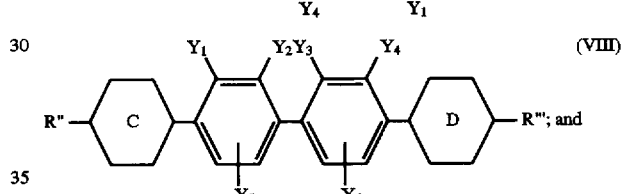

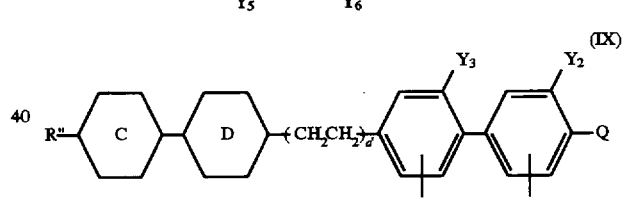

wherein each R″ represents an alkyl group having from 2 to 7 carbon atoms, an alkoxyalkyl group having from 2 to 7 carbon atoms, a mono or difluoroalkyl group having from 2 to 7 carbon atoms, or an alkenyl group having from 2 to 7 carbon atoms, a and a' are, respectively, 0 or 1,

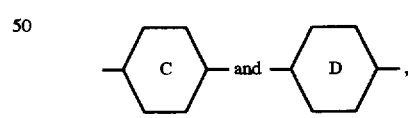

respectively, represent a trans-1-sila-1,4-cyclohexylene group, a trans-4-sila-1,4-cyclohexylene group or a trans-1,4-cyclohexylene group, Q represents CN, F, Cl, $CF_3$, $OCH_2F$, $CClF_2$, $CHClF$, $OCF_3$, $OClCF_2$, $OCHF_2$, $OCHClF$, $(O)_kCT=CX_1X_2$ wherein k is 0 or 1, T and $X_1$ independently represent H, F or Cl, and $X_2$ represents F or Cl, $O(CH_2)_i(CF_2)_jG$ wherein i and j are, respectively, 0, 1 or 2 provided that i+j=2, 3 or 4, and G represents H, F or Cl, or R″ or OR″ wherein R″ is as defined above, $Y_1$ to $Y_6$ are, respectively, H or F, and R‴ is same as R″.

15. A liquid crystal display device which comprises the liquid crystal composition defined in claim 14.

* * * * *